United States Patent [19]
Takaichi et al.

[11] Patent Number: 5,455,235
[45] Date of Patent: Oct. 3, 1995

[54] FOOD COMPOSITION FOR INHIBITING THE FORMATION OF AN INTESTINAL PUTREFACTIVE PRODUCT

[75] Inventors: Akihisa Takaichi, Naruto; Toshihiko Okamoto, Tokushima; Yoshihide Azuma, Naruto; Yoshinari Watanabe, Tokushima; Toshiaki Matsumoto, Tokushima; Katsuya Miyata, Tokushima; Shuichi Sakamoto, Kurume; Hiroshi Okamatsu, Kurume; Megumi Kumemura, Kurume, all of Japan

[73] Assignee: Otsuka Pharmaceutical Co., Ltd., Tokyo, Japan

[21] Appl. No.: 162,209

[22] PCT Filed: Apr. 2, 1993

[86] PCT No.: PCT/JP93/00436

§ 371 Date: Feb. 9, 1994

§ 102(e) Date: Feb. 9, 1994

[87] PCT Pub. No.: WO93/20718

PCT Pub. Date: Oct. 28, 1993

[30] Foreign Application Priority Data

Apr. 10, 1992 [JP] Japan .................................. 4-091185

[51] Int. Cl.$^6$ .................................. A23L 1/30; A23L 2/26; A23L 2/40; A23G 3/00
[52] U.S. Cl. .................................. 514/54; 424/43; 424/44; 424/439; 426/590; 426/599; 426/804
[58] Field of Search .................................. 424/43, 44, 439; 426/590, 599, 804; 514/54

[56] References Cited

U.S. PATENT DOCUMENTS

| | | | |
|---|---|---|---|
| 3,730,737 | 5/1973 | Harvey et al. | 229/75 |
| 4,298,619 | 11/1981 | Mutai et al. | 426/599 |
| 4,678,661 | 7/1987 | Gergely et al. | 514/819 |
| 4,704,269 | 11/1987 | Korab | 514/819 |
| 4,783,331 | 11/1988 | Alexander et al. | 424/44 |
| 4,859,488 | 8/1989 | Kan et al. | 426/658 |
| 5,051,270 | 9/1991 | Ueda et al. | 426/574 |
| 5,087,442 | 2/1992 | Takaichi et al. | 424/44 |
| 5,089,401 | 2/1992 | Fujita et al. | 435/97 |
| 5,130,239 | 7/1992 | Hara et al. | 435/97 |
| 5,160,728 | 11/1992 | Takaichi et al. | 424/44 |
| 5,294,458 | 3/1994 | Fujimori | 426/635 |
| 5,296,473 | 3/1994 | Hara et al. | 514/61 |

FOREIGN PATENT DOCUMENTS 447125  9/1991  European Pat. Off. .

*Primary Examiner*—Ronald W. Griffin
*Attorney, Agent, or Firm*—Sughrue, Mion, Zinn, Macpeak & Seas

[57] ABSTRACT

The present invention provides a food composition for inhibiting the formation of an intestinal putrefactive product, containing lactosucrose as an effective component. This food composition is low in calorific value because the lactosucrose is indigestible, and can decrease the amount of an putrefactive product to be generated in intestines. Accordingly, this food composition effectively prevents the outbreak of a variety of cancers for which the putrefactive product might serve as a promoter.

2 Claims, No Drawings

FOOD COMPOSITION FOR INHIBITING THE FORMATION OF AN INTESTINAL PUTREFACTIVE PRODUCT

TECHNICAL FIELD

The present invention relates to a novel food composition for inhibiting the formation of an intestinal putrefactive product.

BACKGROUND ART

It is known that skatole, indole, p-cresol, 4-ethylphenol and the like are intestinal putrefactive product derived from tryptophan, tyrosine and the like, and may be promotors of a variety of cancers. It is therefore desired to inhibit such components from being formed in intestines.

It is a main object of the present invention to provide a food composition for inhibiting the formation of an intestinal putrefactive product, which can reduce the amount of a harmful putrefactive product to be formed in intestines.

It is another object of the present invention to provide a food composition for inhibiting the formation of an intestinal putrefactive product, which can inhibit an effective component from being decomposed to enhance the stability of the effective component.

DISCLOSURE OF THE INVENTION

After hard study for achieving the objects above-mentioned, the inventors have found the following surprising fact, based on which the present invention has been completed. That is, the intake of lactosucrose can not only reduce the amount of a putrefactive product such as p-cresol, skatole, indole or the like to be generated in human stool, but also lowers the rate of detection, in stool, of germs which contribute to the formation of such a putrefactive product.

More specifically, the present invention provides a food composition for inhibiting the formation of an intestinal putrefactive product, which contains lactosucrose as an effective component.

Lactosucrose is oligosaccharide and can accelerate the propagation of intestinal bifid bacteria, thus reducing the amount of the putrefactive product above-mentioned to be formed. Further, lactosucrose is indigestible and therefore very low in calorific value. Accordingly, lactosucrose is suitable for low-caloric food. The food composition of the present invention containing lactosucrose as an effective component, is fully satisfactory in view of taste, odor, dietary feeling and the like.

Lactosucrose used in the present invention is O—β—D—galactopyranosyl—(1→4)—O—α—D—glucopyranosyl—(1←2)—S—D—fructofuranoside, represented by the following formula:

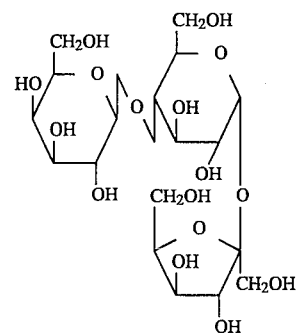

There may be used such a substance which is produced by a conventional producing method. Examples of the conventional producing method include (1) a method discussed in Japanese Patent Publication No. 57-58905 in which, for example, levan sucrase originating from genus Aerobacter, is acted on a solution of sucrose and lactose, (ii) a method discussed in Japanese Patent Unexamined Publication No. 64-85090 in which an extract of cells from the specific genus sporobolomyces, are used, and (iii) a method discussed in Japanese Patent Unexamined Publication No. 2-35095 in which germs of the genus Rohnella are used. In the present invention, lactosucrose produced by any of these methods may be used as it is, or as refined by column chromatography.

The food composition of the present invention is not limited in form, but may be used in the form of a block, a liquid, a sirup, powder or the like. Further, the food composition of the present invention may suitably contain extenders, sweetners, vitamins, cells of bifid bacteria and the like. From the food composition of the present invention, there may be formed (i) a liquid or powdery sweetner such as sirup, table sugar or the like, (ii) a drink such as a refreshing drink, a milk beverage or the like, (iii) block confectionery such as breads, cookies, solid nutritious food (e.g., "Calorie Mate" manufactured by Otsuka Pharmaceutical Co., Ltd.), (iv) sweets such as candies or the like, and (v) healthful food.

In view of the effect of inhibiting the formation of a harmful putrefactive product, the taste and odor as food, and compatibility with other components, the concentration of lactosucrose as an effective component is normally preferably in the range from about 0.5 to about 70 g for 100 g of the food composition. However, the concentration of lactosucrose varies with the form of food to be used. It is therefore required to suitably determine the concentration of lactosucrose within the range above-mentioned for each food.

BEST MODE FOR CARRYING OUT THE INVENTION

When the food composition of the present invention is used in the form of a drink, lactosucrose may be contained in an amount of 0.5 to 30 g, preferably 1 to 15 g, for 100 ml of such a drink.

Such a drink is often an acid drink of which pH is not greater than 4. Accordingly, when lactosucrose is blended with such a drink, the lactosucrose is decomposed with the passage of time. On the other hand, in a neutral drink of which pH is greater than 4, the lactosucrose is gradually decomposed. However, the self-decomposition of lactosucrose causes pH to be lowered, so that a decomposing reaction is accerelated from a certain point of time.

In a drink containing lactosucrose, to restrain pH from being lowered to stably maintain the lactosucrose for a long period of time, the present invention uses a buffer solution to maintain pH in the range from 4.0 to 6.5, preferably from 4.5 to 6.0. If pH is too low, lactosucrose is liable to be decomposed. On the other hand, as pH is increased, the drink is liable to lack an organic refreshing feeling. It is therefore preferable to set pH in the range above-mentioned. When carbonic acid is added, a refreshing feeling is increased and sterilizing conditions such as heating temperature and time can be relaxed, thus further improving the stability of lactosucrose.

As the buffer agent, there may be used a mixture solution containing a weak acid having a buffer function and its salt. The weak acid and its salt may be blended with a drink composition such that the drink composition presents the target pH.

Examples of the weak acid include citric acid, tartaric acid, lactic acid, malic acid, carbonic acid and the like. Examples of the weak acid salt include sodium citrate, sodium tartrate, sodium malate, calcium lactate, sodium lactate, sodium hydrogenphosphate, sodium carbonate, sodium hydrogencarbonate and the like.

A buffer agent comprising a weak acid and its salt, may be blended in such a necessary amount as to maintain pH of the drink composition in the range above-mentioned. That is, the blending amount of the buffer agent is suitably determined according to the type of a drink composition, but may be in the range preferably from 0.03 to 2% by weight and more preferably from about 0.05 to about 0.3% by weight.

As far as the drink composition of the present invention contains factosucrose as an effective component, any of a variety of glucides and sweetners may be added as done in normal drinks. Examples of the glucide component include (i) a variety of saccharides including a monosaccharide such as glucose, fructose and the like, and a disaccharide such as maltose, sucrose and the like, (ii) polysaccharide such as dextrin, cyclodextrin and the like, and (iii) sugar alcohols such as xylitol, erythritol, sorbitol and the like. Examples of the sweetening agent include natural sweetnets (thaumatin, an extract of stevia, a glycyrrhizin), and synthetic sweetners (saccharin, aspartame and the like). These glucide components and sweetners may be blended in an amount of normally 15% by weight or less and preferably 13% by weight or less.

In addition to the components above-mentioned, there may be blended, as necessary, (i) juice of fruit (concentrated juice of fruit) such as grapefruit, apple, orange, lemon, pineapple, banana, pear, grape or the like, (ii) amino acids (sodium glutamate, glycine, alanine, sodium aspartate and the like), (iii) an inorganic electrolyte serving as a mineral source (sodium chloride, potassium chloride, magnesium chloride, magnesium carbonate, calcium chloride and the like), (iv) vitamins and (v) flavor.

The present invention may provide a low-caloric drink composition containing a predetermined amount of lactosucrose. More specifically, the low-caloric drink composition of the present invention contains an inorganic electrolyte component and an organic acid component, and also contains lactosucrose of which amount is in the range from 0.5 to 10 g, preferably from 2 to 7 g for 100 ml of the drink composition. The drink composition also contains an extract of stevia in an amount of 2 to 15 mg per mEq/l of inorganic electrolyte cations in the inorganic electrolyte component above-mentioned.

Since this low-caloric drink composition contains lactosucrose, the amount of a putrefactive product to be formed in the intestines can be reduced. Further, this drink composition is low in calorific value since lactosucrose is indigestible oligosaccharide. Further, when an extract of stevia is blended as a sweetner, it is possible to eliminate or considerably reduce the use of a natural glucide component. Accordingly, the low-caloric drink composition of the present invention can be considerably lowered in caloric value. That is, the caloric value of 100 ml of the drink composition can be lowered to 25 kcal or less, preferably 15 kcal or less. The low-caloric drink composition of the present invention is preferably arranged to prevent the osmotic pressure from being excessively increased such that the osmotic pressure is in the range from 160 to 300 mOsmols, preferably from 200 to 270 mOsmols, which is good in view of absorption.

The inorganic electrolyte component blended with the low-caloric drink composition, may be used for resupplying inorganic electrolyte cations and anions to be lost due to sweating. As the inorganic electrolyte component, there may be used any of a variety of inorganic electrolyte components conventionally used in such a drink composition. Examples of the inorganic electrolyte component include salts of inorganic acids of alkali metals and alkaline earth metals such as $NaCl$, $KCl$, $MgCl_2$, $MgSO_4$, $MgCO_3$, $CaCl_2$, $CaSO_4$, $Na_2SO_4$, $K_3PO_4$, $Ca_3[PO_4]_2$, $KH_2PO_4$, $KH_2PO_4$, $CaHPO_4$ and the like. Normally, a combination of several types of these substances may be used. Generally, magnesium salt and/or calcium salt are blended together with sodium salt and potassium salt. Such inorganic electrolyte components may be selected with consideration taken on the resupply of the inorganic electrolyte cations and anions such as chloride ions, phosphate ions and the like.

The inorganic electrolyte cations may be blended not only in the form of an inorganic electrolyte, but also in the form of an organic acid salt. Examples of the organic acid salt include salts of citric acid, lactic acid, L-glutamic acid, succinic acid, aspartic acid, alginic acid, malic acid, gluconic acid and the like. More specifically, examples of the organic acid salt include sodium citrate, calcium citrate, sodium lactate, calcium lactate, sodium succinate, disodium succinate, sodium glutamate, sodium aspartate, calcium aspartate, sodium alginate, sodium malate, calcium gluconate and the like.

The inorganic electrolyte components and the organic acid salt may be blended in such necessary amounts as to resupply the inorganic cations and anions to be lost due to sweating. The blending amounts may be suitably determined according to the formulation of a usual drink composition. However, 1000 ml of the drink composition contains preferably about 10 to about 40 mEq, more preferably about 20 to about 30 mEq, of inorganic cations, and about 10 to about 25 mEq of inorganic anions.

The organic acid component may be blended in the form of the organic acid salt above-mentioned or in the form of a free acid. Further, the organic acid and the salt thereof may be simultaneously blended. As the organic acid or the salt thereof, there may be used any of the organic acids and the salts mentioned as the organic acid salts. The blending amount of the organic acid component is not limited to a specific value, and may be substantially equal to the amount which is blended in a usual drink composition. However, the organic acid component may be blended in a greater or smaller amount as necessary. Generally, it is preferable to blend the organic acid component in the range from 1.3 to 2.5 g for 1000 ml of the drink composition.

The low-caloric drink composition may contain, together with an inorganic electrolyte component and an organic acid component, an extract of stevia serving as a sweetening agent. The extract of stevia is a sweetner extracted from stevia which is a perennial plant of Compositae. For example, this extract is discussed in Japanese Patent Unexamined Publication No. 52-83731, Japanese Patent Publication No. 58-56628 and the like. According to the present invention, there may be used any of a variety of conventional extracts of stevia discussed in these publications. Preferably, there may be used rebaudioside A, rebaudioside B, rebaudioside C, rebaudioside D, rebaudioside E and glycosylstevioside. Of these, rebaudioside A is more preferable.

The extract of stevia may be blended in an amount of 2 to 15 mg, preferably 2.5 to 10 mg, per mEq/l of inorganic electrolyte cations. By blending the extract of stevia in the range above-mentioned, a bad aftertaste such as a bitter taste, a harsh taste, an astringent taste or the like resulting from the inorganic electrolyte cations, can be eliminated to provide a delicious taste in a satisfactory manner. Further, no adverse effect is exerted to the stability of such a delicious taste, thus enabling the delicious taste to be preserved for a long period of time.

Further, a natural glucide component such as sucrose, glucose, frutose or the like may be suitably blended with calory and osmotic pressure taken into consideration. Normally, such a natural glucide component may be blended in an amount of not greater than 30 g, preferably not greater than 25 g, for 1000 ml of the drink composition.

The low-caloric drink composition of the present invention may contain one or more substances selected from the group consisting of: juice of fruit (concentrated juice of fruit ) such as grapefruit, apple, orange, lemon, pineapple, banana, pear or the like; vitamins; flavor; amino acids such as sodium glutamate, glycine, alanine, sodium aspartate and the like; food fibers such as polydextrose, pectin, xanthan gum, gum arabic, alginic acid and the like; a delicious-taste component such as a glutamic acid, an inosinic acid or the like; and oligosaccharide.

The food composition of the present invention may also be used as a healthful drink composition containing, as effective components, lactosucrose, polydextrose and carotenoid. More specifically, such a healthful drink composition contains 0.5 to 10 g of lactosucrose, 1 to 20 g of polydextrose and 0.5 to 30 mg of carotenoid, for 100 ml of the healthful drink composition.

Further, the healthful drink composition of the present invention may contain, in addition to the components above-mentioned, 0.5 to 20 mg of vitamin E, 10 to 1000 mg of vitamin C and 1 to 15 g of glucide, for 100 ml of the healthful drink composition.

When such a healthful drink composition is drunk, both carotenoid and polydextrose can be ingested. This not only provides improvements in eating habits which are liable to be irregular, and in health conditions, but also prevents fatness, an outbreak of diseases of adult people and the like. This also eliminates a danger of the production of a cancer and provides immunity invigoration. Further, this is effective in prevention of ultraviolet rays and in improvements in constipation. Further, the presence of lactosucrose lowers the amount of an intestinal putrefactive product to be formed. This is further effective in prevention of the production of a cancer and in reinforcement of the immunological system. Also, such a healthful drink composition is fully satisfactory in view of taste, odor and dietary feeling.

Thus, the healthful drink composition of the present invention is useful for maintaining the moderns healthy. In particular, this healthful drink composition is very suitable for those who often take their meal out, who have a less oppotunity of eating vegitables, who are highly oriented to health, and who are liable to be constipated. Further, since this healthful drink composition can be readily taken, this healthful drink composition is suitable for the moderns who are very busy. Also, this healthful drink composition is suitable as a nutritional supplementary drink for an old person or a person under medical treatment due to diseases of adult people or the like.

As the carotenoid, there may be used any of a variety of substances known in the fields of food, medical and pharmaceutical products, and the like. There may be used carotenoid obtained by refining natural substances (palm carotene, dunalella carotene and the like), and synthetic substances thereof. Further, there may be used, as it is, powder or extract of any of plants and animals containing, singly or in combination, carotenoids such as $\alpha$-, $\beta$- and $\gamma$-carotene, lycopene, lutein, canthaxanthin and the like. Of these, $\beta$-carotene is more preferable.

The carotenoid may be blended in an amount of 0.5 to 30 mg, preferably 1 to 10 mg, with 100 ml of the drink composition. If the blending amount of carotenoid exceeds the range above-mentioned, this disadvantageously deteriorates the flavor and lowers the dispersion and solubility of carotenoid.

Carotenoid is oil-soluble. Accordingly, it is required to use oil (edible oil material) for dissolving carotenoid, and an emulsifier for emulsifying the same. As these oil and emulsifier, there may be used any of oils and emulsifiers conventionally used in a variety of foods without particular restrictions imposed therein. Specific examples of the oil include soybean oil, rapeseed oil, rice oil, cotton seed oil, safflower oil, sesame oil, corn oil, peanut oil, sunflower oil, palm oil and the like. Examples of the emulsifier include polyglycerol esters of fatty acids, glycerol esters of fatty acids, propylene glycol of fatty acids, sucrose of fatty acids, soybean phospholipid and the like.

As the polydextrose, there may be used, for example, a series of polysaccharides found by Pfizer Central Research Laboratories. These polysaccharides may be produced, for example, by heat-polymerizing glucose in the presence of acid and polyol serving as a plasticizer. Products of such polysaccharides are commercially available.

Such polydextrose may be generally blended in an amount of 1 to 20 g, preferably 3 to 10 g, with 100 ml of the drink composition. If the blending amount of polydextrose exceeds the range above-mentioned, this disadvantageously deteriorates the flavor and increases the viscosity of the drink composition to deteriorate the feeling of passage through the throat. This also causes an outbreak of diarrhoea.

As far as the healthful drink composition of the present invention contains, as effective components, lactosucrose, polydextrose and carotenoid, no restrictions are imposed on other components to be added. Thus, a variety of sweetening agents and glucides may be blended as done in a usual drink composition. Examples of the glucide include (i) a variety of saccharides including a monosaccharide such as glucose, fructose and the like, and a disaccharide such as maltose, sucrose and the like, (ii) polysaccharide such as dextrin, cyclodextrin and the like, and (iii) sugar alcohols such as xylitol, sorbitol, erythritol and the like. As the sweetners, there may be advantageously used, in addition to the glucides above-mentioned, natural sweetners (thaumatin, an extract of stevia (ribaudioside A or the like), a glycyrrhizin and the like), and synthetic sweetners (saccharin, aspartame and the like). These glucides may be generally blended in an amount of about 1 to about 15 g, preferably about 3 to about 12 g, with 100 ml of the drink composition.

Further, the healthful drink composition of the present invention may suitably contain a variety of nutritive elements, vitamins, minerals (electrolytes), synthetic and natural flavors, coloring agents, flavor materials (cheese, chocolate and the like), pectinic acid and the salts thereof, alginic acids and the salts thereof, organic acids, thickening agents serving as protective colloid substances, pH adjusting agents, stabilizing agents, preservatives, glycerols, alcohols, effervescent ingredients for carbonic drinks and the like. To make the healthful drink composition in the form of a fruit-juice drink or vegetable drink, natural fruit juices or fruit fractions may be added singly or in combination. Each of these additives is not limited in amount, but may be generally added in an amount of 0 to 20 parts by weight for 100 parts by weight of the drink composition.

As the vitamins, there may be used a variety of water-soluble or oil-soluble vitamins such as retinol palmitate, bisbenthiamine, riboflavin, pyridoxine hydrochloride, cyanocobalamin, sodium ascorbate, nicotinamide, calcium pantothenate, folic acid, biotin, cholecalciferol, choline bitartrate and the like. Of these, there are preferably used vitamin E and/or vitamin C from which an anti-cancer action is expected because of their anti-oxidation.

As the minerals (electrolyte trace elements), there may be used usual minerals such as sodium chloride, sodium acetate, magnesium sulfate, magnesium chloride, calcium chloride, dipotassium hydrogen phosphate, sodium dihydrogen phosphate, calcium glycerophosphate, sodium ferrous citrate, manganese sulfate, copper sulfate, zinc sulfate, sodium iodide, potassium sorbate, zinc, manganese, copper, iodine, cobalt and the like. The blending amounts of these minerals may be suitably determined as necessary.

The healthful drink composition of the present invention may be prepared by simultaneously mixing the components above-mentioned, but is preferably prepared by previously dissolving carotenoid in oil, preparing an aqueous solution containing the carotenoid thus dissolved, polydextrose and other additives, and emulsifying the aqueous solution with the use of an emulsifier. More specifically, a solution in which carotenoid has been dissolved in oil, is added to a mixture liquid containing water and a suitable emulsifier, and the resulting mixture is emulsified. Then, the resulting emulsion is mixed with an aqueous solution containing polydextrose and other additives, thus preparing the healthful drink composition of the present invention.

The mixing operation may be conducted at room temperature, but preferably conducted at slightly raised temperature. According to a usual method, the emulsification may be carried out by either a perfect passing system or a cycling system with the use of a suitable emulsifying machine such as a homomixer, a high-pressure homogenizer or the like.

An emulsion obtained after emulsification may be filtered according to a usual method. A suitable container may be charged with the resulting filtrate, and then sterilized, thus providing a desired drink product. The sterilization may be carried out by heat sterilization or aseptic sterilization. To prepare a carbonated beverage, there may be employed a method by which carbonic acid gas is put, under pressure, into the emulsion in the usual way.

The food composition of the present invention may be made in the form of an effervescent preparation which preferably contains about 20 to about 50% by weight of lactosucrose.

The effervescent preparation contains sodium hydrogencarbonate and/or sodium carbonate as an effervescent component, and a neutralizing agent (e.g., an organic acid). The blending amount of the effervescent component may be suitably determined according to the shape and purpose of the effervescent preparation. To obtain good effervescent properties, 8 to 60% by weight, preferably 10 to 35% by weight, of the effervescent component may be blended. In particular, it is desired to blend 9 to 50% by weight, preferably 22 to 26% by weight, of sodium carbonate, and/or 8 to 50% by weight, preferably 20 to 45% by weight, of sodium hydrogencarbonate.

As an organic acid serving as the neutralizing agent, there may be used one or more substances selected from the group consisting of citric acid, tartaric acid, fumaric acid, ascorbic acid, lactic acid and malic acid. The blending ratio of the neutralizing agent is suitably determined according to the concentration of the effervescent component. Normally, the neutralizing agent may be contained, in the effervescent preparation, in the range from 10 to 70% by weight, preferably from 20 to 50% by weight and more preferably from 30 to 40% by weight. In particular, it is preferable to use the neutralizing agent in an equivalent amount or more for sodium hydrogencarbonate or the like.

When the effervescent preparation of the present invention obtained by blending the effervescent component and the neutralizing agent (organic acid), is dissolved in water, pH of the solution becomes acid and the effervescent preparation presents a good solubility. Also, carbonic acid gas is sufficiently generated and the aqueous solution presents a good taste.

The effervescent preparation of the present invention may contain a variety of medicines such as vitamins, iron salt, other inorganic salts and a glucide according to the usage object. In addition to the medicines above-mentioned, a variety of additives may be blended as necessary. Examples of the additives include a binder, an excipient, a lubricant, a thickening agent, a surfactant, an osmotic-pressure adjusting agent, an electrolyte, sweetening agents, flavers, coloring matter, a pH adjusting agent and the like.

The effervescent preparation of the present invention may be produced by adding potassium carbonate in a method similar to the usual method of producing an effervescent preparation. That is, the effervescent preparation may be produced by a direct powder compressing method, a dry or wet granule compressing method.

The effervescent preparation is not particularly limited in shape, but may be made in such a suitable shape as to be used as dissolved and dispersed in water, such as a granule, powder, a capsule or the like, in addition to a tablet.

When the effervescent preparation is dissolved in water, the resulting solution is made in the form of a drink suitable for oral administration. The dosage may be suitably determined according to the usage object, and the age, gender, weight, disease degree of a living body which takes the effervescent preparation. For oral administration, there may be administered, at one time, about 1.5 to about 6 g of the effervescent preparation as dissolved in 100 to 300 ml of water.

The food composition of the present invention may serve as high-protein and highly-viscous nutrition resupply food to be suitably taken after physical exercise such as athletics, aerobics, cycling, marathon, triathlon, Spartathlon and the like. Such food may be produced by the usual producing method.

The food composition of the present invention may also be applied to a drink containing an oligopeptide mixture and to drop (chewable) confectionery.

When applying to drop (chewable) confectionery, the food composition of the present invention may be used in any of a variety of forms from particles to pellets. Such drop confectionery may contain 10 to 70% by weight of lactosucrose. More specifically, 0.2 to 5 g of a drop preferably contains about 0.1 to about 3 g of lactosucrose.

Lactosucrose may be used singly as a refined substance as mentioned earlier, but may also be used, in the course of production, as a mixture containing unreacted monosaccharide, disaccharide, oligosaccharide or the like.

To make drop confectionery, a lubricant is preferably added. Examples of the lubricant include sugar-ester, magnesium stearate, talc, synthetic aluminium silicate, fine powder of silicon oxide, starch, sodium lauryl sulfate, boron, magnesium oxide, higher fatty acid, higher alcohol, macrogol, silicon, polyoxyethylene glycol fatty ester and the like. The blending amount of the lubricant is preferably in the range from 0.3 to 3% by weight for drop confectionery. As other components, there may be suitably added vitamins, flavors, sweetening agents, fruit juice and the like.

In particular, drop confectionery preferably gives a feeling of refreshment in the mouth. In this connection, 1-menthol, cinnamon, lemon flavor, orange flavor or the like may be added with usual means. Also, when the effervescent component mentioned earlier is blended, the drop confectionery may generate a more refreshing feeling in the mouth.

The drop confectionery may be produced in the form of a tablet by mixing the components above-mentioned and subjecting the resulting mixture to conventional means such as a direct powder compressing method, a granule compressing method, a wet molding method or the like.

The food composition of the present invention is not particularly limited in intake amount. However, about 0.03 to 0.6 g of lactosucrose per 1 kg of body weight may be generally taken per day.

Industrial Applicability

The food composition of the present invention contains lactosucrose as an effective component. Accordingly, the food composition taken in a human body accelerates an increase in bifid bacteria. This reduces the amount of putrefactive product such as p-cresol, skatole, indole, 4-ethyl phenol or the like to be generated in the intestines. Thus, this is effective in prevention of any of a variety of cancers for which such an intestinal putrefactive product might be a promotor. In the food composition of the present invention, lactosucrose which is an effective component, is indigestible oligosaccharide and low in calorific value. Accordingly, the food composition of the present invention may be suitably used as low-caloric food.

EXAMPLES

The following description will discuss the food composition of the present invention with reference to examples thereof. It is a matter of course that the present invention is not limited to these examples only.

Test Example

According to the following method, there were measured variations of the amount of a putrefactive product in fecal matter by the administration of lactosucrose of the present invention.

(1) Matter to be Tested

As raw materials, sucrose and lactose were mixed to prepare a mixture, on which S-fructofranosidase was acted. Through respective steps of decoloration, desalinization, filtration and drying, there was prepared a powder preparation containing 59.0% by weight of lactosucrose (hereinafter referred to as LS55P). The LS55P contained 59.0% by weight of lactosucrose, 22.7% by weight of lactose, 8.4% by weight of sucrose, 1.6% by weight of fructose, 0.8% by weight of glucose, 6.8% by weight of other sugar, and 0.8% by weight of water.

(2) Persons to be Tested

As persons to be tested, there were designated 13 chronically constipated long-stay patients of 55 years and over who had basal diseases such as cerebral infarction, diabetes mellitus and the like. Eleven patients out of these 13 patients had been addicted to the use of a laxative before the test started. During the test period, the dosages of such a laxative were minimized in order to make the physiological operations of these patients highly precise.

(3) Intake of the Matter to be Tested

The test period extended over four consecutive weeks. The first one week served as a control period during which the matter to be tested was not taken, and the three weeks subsequent to the control period, served as an intake period during which the matter to be tested was taken. The daily dosage of the LS55P was set to 0.32 g/kg B.W. Throughout the intake period, the matter to be tested, to be daily taken was divided into two equal portions, which were taken, as dissolved in about 100 ml of city water, at 10 am and 3 pm, respectively, by each person to be tested.

(4) Analysis

After each evacuation of each person to be tested, the fecal matter and the urine were separated from each other, and all the amount of fecal matter was collected and measured for weight. After fully kneaded and made homogenous, each fecal matter was preserved under conditions of not greater than −30 ° C. and subjected to analysis of putrefactive product therein. Such analysis was conducted for all fecal matter evacuated during the test period.

After the fecal matter and the putrefactive product therein were subjected to variance analysis in a two-way layout, a significant test was conducted on the concentration of the putrefactive product in the fecal matter and the amount of the fecal matter by the Tukey multiple comparison method.

(5) Measuring Method and Results

The putrefactive product in the fecal matter, i.e., p-cresol, 4-ethylphenol, indole and skatole were analyzed according to the following method.

About 2 g of each fecal matter as precisely measured, was put in a 200-ml Kjeldahl flask, and about 10 ml of purified water was added to the flask, which was then fully suspended. A suitable amount of 2N-sodium hydroxide solution was added to each resulting suspension to adjust pH in the range from 8.5 to 9.0. The solution was then subjected to steam distillation, and about 95 ml of distillate was collected. Purified water was added to this distillate such that the total amount was accurately equal to 100 ml. The distillate was then analyzed for a putrefactive product with the use of gas chromatography mass analyzer (GC-14A gas chromatography interfaced with a GC—MS QP1000EX mass spectrometer manufactured by Shimazu Corporation). The following shows the analyzing conditions:

Column: SHIMAZU HiCAP CBP1-M25-025
   Carrier gas: Helium 0.75 kg/cm$^2$
   Inlet port temp.: 250 °C.
   Column temp.: 50° to 200 °C. (30 °C./min.)
   Ionization method: EI
   Ionization voltage: 70 eV
   Separator temp.: 270 °C.
   Ion source temp.: 250° C.

After the analysis of the putrefactive product in each fecal matter, there was calculated, for each person to be tested, the total amount of the putrefactive products during the control period, during the first intake week, during the second intake week and during the third intake week. This total amount was regarded as the amount of the putrefactive products evacuated in the fecal matter. For each person to be tested, the concentration of the putrefactive product in fecal matter was calculated from this evacuated amount of putrefactive product and the total weight of the fecal matter evacuated during the test periods. Table 1 shows variations of the concentration of the putrefactive product in the fecal matter and the amount of the putrefactive product.

The results are shown in terms of the averages ±standard deviation. In Table 1, significant differences P with respect to the values in the control periods are shown in the following manner. That is, "*" represents that P is smaller than 0.05, "" represents that P is smaller than 0.01 and "*" represents that P is smaller than 0.001.

In Table 1, the amount of putrefactive product per 1 g of fecal matter is shown in the upper row, while the amount of putrefactive product evacuated in the fecal matter per week is shown in the lower row.

TABLE 2-continued

| Example No. | 1 | 2 | 3 | 4 | 5 | 6 |
|---|---|---|---|---|---|---|
| Total Anion (mEq/l) | 27.5 | 21.5 | 27.5 | 22.5 | 13.5 | 33.5 |
| Cl$^-$ | 16.5 | 10.5 | 16.5 | 10.5 | 6.5 | 17.5 |
| Citric acid ion (—) | 10 | 10 | 8 | 10 | 4 | 11 |
| Lactic acid ion (—) | 1 | 1 | 1 | 2 | 1 | 1 |
| Tartaric acid ion (—) | 0 | 0 | 1 | 0 | 1 | 2 |
| Malic acid ion (—) | 0 | 0 | 1 | 0 | 1 | 2 |
| Total | 27.5 | 21.5 | 27.5 | 22.5 | 13.5 | 33.5 |
| Rebaudioside A (mg/l) | 80 | 75 | 83 | 73 | 70 | 85 |
| Sugar (g/l) | | | | | | |
| Fructose | 20 | 18 | 17 | 16 | 15 | 22 |
| Glucose | 2 | 1 | 2 | 3 | 2 | 1 |
| Lactosucrose (g/l) | 10 | 50 | 10 | 60 | 20 | 20 |

Example 7 (Effervescent Preparation)

| (Component) | (% by weight) |
|---|---|
| LS55P | 34 |
| L-ascorbic acid | 21 |
| L-tartaric acid | 20 |
| Sweetening agents | Suitable quantity |
| Sodium hydrogencarbonate | 21 |
| Sodium chloride | Suitable quantity |
| Potassium carbonate | 0.5 |
| Flavor, Coloring agent | Small quantity |

TABLE 1

| | | Control Period | First In-take Week | Second In-take Week | Third In-take Week |
|---|---|---|---|---|---|
| p-Cresol | (nmol/gwet) | 449.6 ± 297.0 | 309.1 ± 243.8** | 277.5 ± 218.3*** | 227.1 ± 179.7*** |
| | (μmol/week) | 269.8 ± 148.5 | 224.7 ± 113.8 | 205.4 ± 146.5 | 175.4 ± 113.6 |
| Indole | (nmol/gwet) | 125.4 ± 102.3 | 91.7 ± 63.3* | 89.8 ± 72.0* | 83.3 ± 34.9** |
| | (μmol/week) | 80.9 ± 54.2 | 77.0 ± 48.7 | 80.0 ± 71.7 | 76.7 ± 47.7 |
| Skatole | (nmol/gwet) | 164.7 ± 230.1 | 100.1 ± 185.4 | 74.5 ± 131.0** | 66.2 ± 135.2** |
| | (μmol/week) | 94.6 ± 125.0 | 59.1 ± 87.4 | 56.3 ± 99.1 | 49.0 ± 88.9* |
| 4-Ethylphenol | (nmol/gwet) | 10.3 ± 5.5 | 8.2 ± 5.2 | 10.7 ± 5.9 | 8.5 ± 4.7 |
| | (μmol/week) | 6.9 ± 4.1 | 6.7 ± 4.1 | 8.2 ± 4.1 | 7.1 ± 4.3 |

Examples 1 to 6 (Low-Caloric Drink Composition)

In each of Examples 1 to 6, there was prepared a drink composition having the components set forth in Table 2. Further, suitable flavor and vitamins were blended with the drink compositions. Water was added such that the total amount of each drink composition was equal to 1000 ml.

TABLE 2

| Example No. | 1 | 2 | 3 | 4 | 5 | 6 |
|---|---|---|---|---|---|---|
| Cation (mEq/l) | | | | | | |
| Na$^+$ | 21 | 15 | 21 | 15 | 8 | 27 |
| K$^+$ | 5 | 5 | 5 | 5 | 4 | 5 |
| Ca$^{2+}$ | 1 | 1 | 1 | 2 | 1 | 1 |
| Mg$^{2+}$ | 0.5 | 0.5 | 0.5 | 0.5 | 0.5 | 0.5 |

-continued

| (Component) | (% by weight) |
|---|---|
| | 100 (Total 5 g) |

Tablets were prepared by mixing and directly tableting the components above-mentioned. Also, powder was prepared by mixing, weighing and folding the components above-mentioned. Also, granules were prepared by mixing, weighing, granulating, drying and then folding the components above-mentioned.

The following effervescent preparations were prepared in the same manner as in Example 7.

Example 8 (Effervescent Preparation)

| (Component) | (% by weight) |
|---|---|
| LS55P | 40 |
| L-ascorbic acid | 10 |
| L-tartaric acid | 23 |
| Sweetening agents | Suitable quantity |
| Sodium hydrogencarbonate | 22 |
| Sodium citrate | Suitable quantity |
| Potassium carbonate | 0.4 |
| Flavor, Coloring agent | Small quantity |
| | 100 (Total 5 g) |

Example 9 (Effervescent Preparation)

| (Component) | (% by weight) |
|---|---|
| LS55P | 40 |
| L-ascorbic acid | 11 |
| L-tartaric acid | 23 |
| Sweetening agents | Suitable quantity |
| Ferric ammonium citrate | 0.8 |
| Sodium hydrogencarbonate | 22 |
| Cyanocobalamin | Small quantity |
| Sodium citrate | Suitable quantity |
| Potassium carbonate | 0.4 |
| Flavor, Coloring agent | Small quantity |
| | 100 (Total 4.6 g) |

Example 10 (Effervescent Preparation)

| (Component) | (% by weight) |
|---|---|
| LS55P | 40 |
| L-tartaric acid | 29 |
| Sweetening agents | Suitable quantity |
| Ferric ammonium citrate | 3.6 |
| Sodium hydrogencarbonate | 24 |
| Cyanocobalamin | Small quantity |
| Potassium carbonate | 0.5 |
| Flavor, Coloring agent | Small quantity |
| | 100 (Total 4 g) |

Examples 11 to 18 (Effervescent Preparation)

There were prepared effervescent preparations having the compositions set forth in Table 3, in the same manner as in Examples 7 to 10.

TABLE 3

| Component (%) | Example No. | | | | | | | |
|---|---|---|---|---|---|---|---|---|
| | 11 | 12 | 13 | 14 | 15 | 16 | 17 | 18 |
| LS55P | 40 | 40 | 40 | 60 | 50 | 35 | 45 | 35 |
| L-ascorbic acid | 11 | 11 | 11 | 8 | 10 | 10 | 10 | 13 |
| L-tartaric acid | 23 | 23 | 23 | 13 | 19 | 20 | 20 | 25 |
| Sweetening agent | | | | Suitable Quantity | | | | |
| Sodium hydrogen-carbonate | 22 | 22 | 22 | 15 | 15 | 20 | 20 | 23 |
| Ferric ammonium citrate | 0.8 | 0.8 | 0.8 | 0.8 | 0.8 | — | — | 0.7 |
| Ferric sodium citrate | — | — | — | — | — | 1.2 | — | — |
| Ferric citrate | — | — | — | — | — | — | 0.8 | — |
| Cyanocobalamin | | | | Small quantity | | | | |
| Sodium citrate | | | | Suitable quantity | | | | |
| Flavor & Coloring matter | | | | Suitable quantity | | | | |
| Total Weight (g) | 4.6 | 4.6 | 4.7 | 4.6 | 4.6 | 4.7 | 4.7 | 5.4 |

Examples 19 to 30 (High-protein and Highly-viscous Nutrition Resupply Food)

Sodium caseinate, calcium caseinate, gelatin and LS55P were put in water. After each resulting aqueous solution was stirred to dissolve these components therein, minerals such as NaCl and the like were put in the aqueous solution, which was then stirred to dissolve the minerals, thus preparing a liquid A.

On the other hand, casein was dissolved in water, into which NaOH was added. After NaOH had been dissolved to neutralize each resulting aqueous solution, minerals such as $MgSO_4$, vitamins and oils were added to the solution. Each solution was stirred to dissolve these added substances, thus preparing a liquid B.

Liquid A and liquid B were mixed and stirred. The amount of each resulting mixture was adjusted. Vitamins, flavor and the like were added to each mixture, causing the mixture to be emulsified.

Then, 80 ml of each resulting emulsion was fill in a tube-type container, which was then sterilized, thus providing a product.

Table 4 shows the components and the blending amounts thereof used to prepare the products above-mentioned. The following shows the types of the vitamins and minerals used to prepare the products above-mentioned.

| (Type) | (Blending Amount) |
|---|---|
| I. Vitamins | |
| Vitamin A | 1155 IU |
| Vitamin $B_1$ | 0.92 mg |
| Vitamin $B_2$ | 0.92 mg |
| Vitamin $B_6$ | 0.92 mg |
| Vitamin $B_{12}$ | 2.77 μg |
| Vitamin C | 34.64 mg |
| Vitamin D | 92.36 IU |
| Vitamin E | 6.93 IU |
| Pantothenic acid | 4.62 mg |
| Niacin | 9.24 mg |
| Folic acid | 184.72 μg |
| Biotin | 138.54 μg |
| Vitamin K | 69.27 μg |
| Choline | 115.45 mg |
| II. Minerals | |
| Ca | 230.90 mg |
| $PO_4$ | 230.90 mg |
| Mg | 92.36 mg |
| Na | 323.26 mg |
| K | 600.34 mg |

-continued

| (Type) | (Blending Amount) |
|---|---|
| Cl | 461.80 mg |
| Fe | 7.39 mg |
| Zn | 3.69 mg |
| Cu | 0.46 mg |
| Mn | 9.24 mg |
| I | 34.64 mg |

TABLE 4

| Example No. | 19 | 20 | 21 | 22 | 23 | 24 | 25 | 26 | 27 | 28 | 29 | 30 |
|---|---|---|---|---|---|---|---|---|---|---|---|---|
| Protein Components (g) | | | | | | | | | | | | |
| Casein | 5.0 | 4.9 | 6.9 | 6.7 | 5.6 | 5.6 | 6.9 | 4.9 | 5.0 | 4.9 | 5.6 | 6.3 |
| Sodium caseinate | 2.1 | — | — | 2.2 | 1.1 | — | 1.1 | 1.1 | 3.5 | 3.1 | — | — |
| Calcium caseinate | 3.0 | 3.7 | 3.3 | 3.3 | 1.1 | — | 2.2 | 1.7 | — | — | 2.9 | 3.0 |
| Whole milk powder | — | 4.7 | 3.9 | — | 5.6 | 3.7 | — | 1.5 | 5.6 | 3.5 | 4.3 | 2.5 |
| Skim milk powder | — | 3.0 | 1.5 | — | 2.9 | 1.5 | 1.5 | 0.9 | 1.5 | 1.8 | — | 3.8 |
| Gelatin | 0.8 | — | — | 1.4 | 1.2 | 1.5 | 0.9 | 0.6 | — | 0.4 | 0.7 | 0.2 |
| Gelatin decomposed by enzyme | — | — | 2.2 | — | — | 2.0 | 1.1 | 1.5 | — | — | — | 0.4 |
| Wheat flour | 3.0 | — | — | — | 2.0 | 5.6 | 4.0 | 2.0 | — | 1.0 | 1.4 | 0.8 |
| Cheese | — | 2.7 | 2.0 | — | — | 3.2 | — | 3.8 | 3.2 | 3.6 | 2.4 | — |
| LS55P (g) | 7.0 | 2.4 | 2.7 | 3.0 | 1.7 | 1.7 | 3.3 | 5.7 | 2.0 | 3.5 | 3.5 | 1.7 |
| Lipid Component (g) | | | | | | | | | | | | |
| Rice oil | 4.2 | 0.1 | — | 5.0 | 1.0 | 0.8 | 0.9 | 1.0 | 1.0 | 1.2 | 1.1 | 1.1 |
| Chocolate | — | 3.0 | — | — | — | — | — | — | 3.0 | — | — | 3.3 |
| Other Components | | | | | | | | | | | | |
| Vitamins | | | | | | Suitable quantity | | | | | | |
| Minerals | | | | | | Suitable quantity | | | | | | |
| Flavor | | | | | | Suitable quantity | | | | | | |

Using the oligopeptide mixture set forth in Japanese Patent Unexamined Publication No. 3-272694, there were dissolved, in 1 l of water, the components shown in Table 5 for each of Examples 31 to 33, thus producing an oligopeptide drink.

TABLE 5

| Components to be Blended | Example 31 | Example 32 | Example 33 |
|---|---|---|---|
| Oligopeptide mixture | 25 g | 50 g | 100 g |
| LS55P | 70 g | 70 g | 70 g |
| Rice oil | 42 g | 42 g | 42 g |
| Vitamin A | 11500 IU | 11500 IU | 11500 IU |
| Vitamin $B_1$ | 9.2 mg | 9.2 mg | 9.2 mg |
| Vitamin $B_2$ | 9.2 mg | 9.2 mg | 9.2 mg |
| Vitamin $B_6$ | 9.2 mg | 9.2 mg | 9.2 mg |
| Vitamin $B_{12}$ | 27.7 µg | 27.7 µg | 27.7 µg |
| Vitamin C | 3346.4 mg | 3346.4 mg | 3346.4 mg |
| Vitamin D | 9923.6 IU | 9923.6 IU | 9923.6 IU |
| Vitamin E | 69.31 IU | 69.31 IU | 69.31 IU |
| Pantothenic acid | 46.2 mg | 46.2 mg | 46.2 mg |
| Niacin | 92.4 mg | 92.4 mg | 92.4 mg |
| Folic acid | 1847.2 µg | 1847.2 µg | 1847.2 µg |
| Biotin | 1385.4 µg | 1385.4 µg | 1385.4 µg |
| Vitamin K | 692.7 µg | 692.7 µg | 692.7 µg |
| Choline | 1154.5 mg | 1154.5 mg | 1154.5 mg |
| Ca | 2309.0 mg | 2309.0 mg | 2309.0 mg |
| $PO_4$ | 2309.0 mg | 2309.0 mg | 2309.0 mg |
| Mg | 923.6 mg | 923.6 mg | 923.6 mg |
| Na | 3232.6 mg | 3232.6 mg | 3232.6 mg |
| K | 6003.4 mg | 6003.4 mg | 6003.4 mg |
| Cl | 4618.0 mg | 4618.0 mg | 4618.0 mg |
| Fe | 73.9 mg | 73.9 mg | 73.9 mg |
| Zn | 36.9 mg | 36.9 mg | 36.9 mg |
| Cu | 4.6 mg | 4.6 mg | 4.6 mg |
| Mn | 92.4 mg | 92.4 mg | 92.4 mg |
| I | 346.4 µg | 346.4 µg | 346.4 µg |
| Flavor | | Suitable quantity | |

Examples 34 to 43 (Drink)

In each of Examples 34 to 43, a drink was prepared by mixing the components shown in Table 6 and adding water to the resulting mixture such that the amount of the mixture was equal to 100 ml. In Table 6, "LS75P" refers to a powder preparation containing 75% by weight of lactosucrose (This definition will be also applied in the following description).

TABLE 6

| Example No. | 34 | 35 | 36 | 37 | 38 | 39 | 40 | 41 | 42 | 43 |
|---|---|---|---|---|---|---|---|---|---|---|
| Protein Components (g) | | | | | | | | | | |
| Casein | 3.3 | 4.5 | — | — | — | — | — | — | — | — |
| Sodium caseinate | — | — | 2.2 | 2.6 | 3.3 | 4.0 | 2.9 | 2.6 | 3.2 | 3.3 |
| Calcium caseinate | — | — | 1.1 | 0.6 | — | — | — | — | — | — |
| Casein decomposed by enzyme | — | — | 0.7 | 2.2 | — | 0.6 | 0.4 | 1.2 | — | — |
| Soybean protein decomposed by enzyme | — | — | 0.2 | — | 0.5 | 0.2 | — | — | 0.3 | — |
| Gelatin decomposed by enzyme | 2.5 | 3.1 | 2.0 | — | 2.2 | 2.6 | 2.1 | — | 2.0 | 2.1 |
| Glucide Component (g) | | | | | | | | | | |
| LS55P (g) | 15 | 10 | 8 | 10 | 15 | 12 | 15 | 12 | 12 | 10 |
| LS75P | 1.5 | 2 | — | — | 4 | — | 3 | — | — | 2 |
| Lipid Component (g) | | | | | | | | | | |
| Soybean oil | 2.0 | — | — | — | — | 2.4 | — | — | 2.3 | — |
| Rice oil | — | 2.3 | — | 1.2 | — | 1.0 | 1.0 | 2.0 | — | — |
| Cottonseed oil | — | — | 2.2 | — | 1.5 | — | — | — | — | 1.7 |
| Peanut oil | — | — | — | 1.0 | — | — | — | — | — | — |
| Macadamia nut oil | 0.2 | — | — | — | 0.6 | — | 0.7 | — | — | — |
| Other Components | | | | | | | | | | |
| Vitamins | | | | | Suitable quantity | | | | | |
| Minerals | | | | | Suitable quantity | | | | | |
| Flavor | | | | | Suitable quantity | | | | | |

Examples 44 to 50 [Drops (Chewable Tablets)]

In each of Examples 44 to 50, drops (chewable tablets) were prepared by mixing the components shown in Table 7 and subjecting each resulting mixture to a direct powder compressing method.

TABLE 7

(Unit: mg)

| Example No. | 44 | 45 | 46 | 47 | 48 | 49 | 50 |
|---|---|---|---|---|---|---|---|
| LS75P | — | — | — | 700 | 3330 | 600 | 350 |
| LS55P | 1800 | 3600 | 4620 | — | — | — | — |
| Sugar ester | 40 | 80 | 84 | 20 | 80 | 15 | 7 |
| Polydextrose | 150 | 400 | 300 | 100 | 300 | 60 | 60 |
| Sucrose | 100 | 200 | 200 | 20 | 200 | 80 | 20 |
| Vitamin C | 150 | 320 | 200 | 20 | 200 | — | — |
| Powder of orange juice | 80 | 150 | — | — | 100 | 20 | 5 |
| Powder of lemon juice | — | — | 84 | 40 | — | 10 | 5 |
| L-Tartaric acid | — | — | — | — | 460 | 95 | 50 |
| NaHCO$_3$ | — | — | — | — | 500 | 100 | 50 |
| K$_2$CO$_3$ | 30 | 40 | 40 | 40 | 30 | 8 | 8 |
| Flavor, Sweetner Agent | | | Suitable quantity | | | | |
| Tablet Weight | 2400 | 4950 | 5580 | 1000 | 5200 | 1000 | 5000 |

Examples 51 to 59 (Healthful Drink Composition)

In each of Examples 51 to 59, a healthful drink composition was prepared by mixing the components shown in Table 8 and adding water to the resulting mixture such that the amount thereof was equal to 100 ml.

TABLE 8

| Component (in 100 ml) | Example No. | | | | | | | | |
|---|---|---|---|---|---|---|---|---|---|
| | 51 | 52 | 53 | 54 | 55 | 56 | 57 | 58 | 59 |
| β-Carotene (mg) | 3 | 5 | 10 | 15 | 1 | 2 | 30 | 5 | 3 |
| Polydextrose (g) | 5 | 3 | 5 | 7 | 4 | 2 | 10 | 20 | 20 |
| Emulsifier (mg) | 6 | 10 | 20 | 30 | 5 | 6 | 20 | 15 | 8 |
| Oil (mg) | 100 | 90 | 80 | 120 | 50 | 50 | 200 | 70 | 60 |
| Fruit Sugar (g) | — | 15 | 10 | — | 15 | 15 | 15 | 5 | 10 |
| Organic Acid (mg) | | | | | | | | | |
| Citric acid | 200 | 400 | 100 | 300 | 50 | 20 | — | — | — |
| L-Tartaric acid | — | — | 50 | — | 50 | 10 | 100 | 200 | — |
| Lactic acid | — | — | — | — | 50 | 10 | 100 | — | 200 |
| Vitamins | | | | | | | | | |
| L-Ascorbic acid (mg) | 300 | 200 | 100 | 50 | 30 | 150 | 200 | 1000 | 50 |
| Tocopherol (mg) | 10 | 5 | 10 | 20 | 20 | 0.5 | 20 | 10 | 5 |
| LS55P (g) | 2 | 5 | 10 | 3 | 8 | 7 | 5 | 12 | 10 |
| Flavor & Sweetner | | | | Suitable quantity | | | | | |

Examples 60 to 70 (Drink Composition)

In each of Examples 60 to 70, a healthful drink composition was prepared by mixing the components shown in Table 9 and adding water to the resulting mixture such that the amount thereof was equal to 100 ml. In Table 9, each gas volume value refers to an index representing the amount of contained carbon dioxide. Accordingly, as the numeral of gas volume is increased, the amount of contained carbon dioxide is increased. More specifically, the gas volume value is determined such that, when a solution contains gas of carbon dioxide in the same volume as that of the solution, the gas volume value of the solution is equal to 1.

TABLE 9

| Component (in 100 ml) | Example No. | | | | | | | | | | |
|---|---|---|---|---|---|---|---|---|---|---|---|
| | 60 | 61 | 62 | 63 | 64 | 65 | 66 | 67 | 68 | 69 | 70 |
| Lactosucrose (g) | 3 | 12 | 9 | 1 | 8 | 2 | 4 | 10 | 15 | 7 | 13 |
| Glucide (g) | | | | | | | | | | | |
| Isomerized sugar | 8 | — | — | 7 | 7 | 8 | 5 | — | — | 9 | — |
| Sucrose | — | 1 | 8 | 3 | 7 | 5 | 3 | — | — | — | — |
| Fructose | 2 | 6 | — | 1 | — | — | 3 | — | — | — | 4 |
| Glucose | 2 | 2 | — | — | 2 | — | 3 | — | — | 2 | — |
| Buffer agent (mg) | | | | | | | | | | | |
| Citric acid | 3 | 2 | — | — | 8 | — | — | 2 | 5 | — | — |
| Tartaric acid | — | 2 | — | 2 | — | — | — | — | — | 10 | — |
| Malic acid | 4 | — | 8 | — | 5 | — | 4.5 | — | — | — | — |
| Lactic acid | 8 | — | — | 2 | — | 20 | — | — | — | 10 | — |
| Sodium citrate | 20 | 30 | 10 | — | 80 | — | — | 100 | 55 | 70 | — |
| Sodium tartrate | 60 | — | — | 60 | 25 | 70 | — | — | — | 30 | 20 |
| Sodium malate | — | 80 | 150 | — | — | 100 | 45 | — | 10 | — | 50 |
| Calcium lactate | — | — | — | — | 15 | 10 | — | — | — | — | 5 |
| Inorganic Electrolyte (mg) | | | | | | | | | | | |
| Sodium chloride | — | — | 4 | — | 1 | 1.5 | — | — | 2 | — | — |
| Potassium chloride | — | 3 | — | 2 | — | — | 5 | — | 1 | 1 | — |
| Magnesium chloride | 2 | — | 1 | — | — | — | — | — | 1 | — | — |
| Fruit juice (%) | 3 | — | 1 | 0.5 | 0.1 | — | — | — | — | 2 | 0.3 |
| Flavor & Sweetner | | | | | Suitable quantity | | | | | | |
| Gas volume | — | — | — | — | — | 3.0 | 2.0 | 2.5 | 2.3 | 3.3 | 1.5 |
| pH | 5.0 | 6.3 | 5.8 | 4.9 | 5.8 | 5.3 | 5.5 | 5.6 | 6.4 | 5.6 | 5.9 |

What is claimed is:

1. A drink composition for inhibiting the formation of an intestinal putrefactive product, containing lactosucrose in an amount of 0.5 to 30 g/100 ml, a buffer solution being added to said composition such that pH of said composition is adjusted in the range from 4.0 to 6.5.

2. A drink composition according to claim 1, wherein the buffer solution comprises a weak acid having a buffer function and a salt thereof.

* * * * *